US00PP14368P39

(12) United States Plant Patent
Friday

(10) Patent No.: US PP14,368 P3
(45) Date of Patent: Dec. 16, 2003

(54) PEACH TREE NAMED 'P.F. 35-007'

(50) Latin Name: *Prunus persica*
Varietal Denomination: P.F. 35-007

(75) Inventor: Paul Jan Friday, Coloma, MI (US)

(73) Assignee: Paul J. Friday, Coloma, MI (US)

( * ) Notice: Subject to any disclaimer, the term of this patent is extended or adjusted under 35 U.S.C. 154(b) by 0 days.

(21) Appl. No.: 10/051,958

(22) Filed: Jan. 22, 2002

(65) Prior Publication Data

US 2003/0140388 P1 Jul. 24, 2003

(51) Int. Cl.[7] ..... A01H 5/00
(52) U.S. Cl. ..... Plt./198
(58) Field of Search ..... Plt./198

*Primary Examiner*—Bruce R. Campell
*Assistant Examiner*—W C Haas

(57) ABSTRACT

A new and distinct variety of peach *Prunus persica,* tree having the following unique combination of desirable featres:

1. The new and distinct variety of peach tree is of average height and of upright growth and a regular and productive bearer of peaches.
2. Producing a very firm fruit having a resilient flesh texture.
3. Blossoms are non-showy when in full bloom.
4. A substantially oval spherical fruit with skin of dark red color overlying a yellow which covers approximately fifteen percent (15%) of its surface at maturity.
5. Late maturing fruit of good taste.
6. A late maturing fruit of good storage and shelf life.

1 Drawing Sheet

Botanical classification: *Prunus persica.*

ORIGIN OF VARIETY

The new peach tree (hereinafter referred to as the 'P.F. 35-007' peach tree) was originated by Paul Friday in the experimental orchard, which is maintained for the purposes of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 35-007', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrated that such reproduction of the characteristics of the tree are consistent and are established and transmitted through suceeding propagation.

SUMMARY OF THE VARIETY

The new and distinct variety of peach tree is of average height and of upright growth and a regular and productive bearer of peaches. A distinct characteristic of the 'P.F. 35-007' peach tree is its medium vigor having growth of about twenty-four inches (24") per year. The blossoms bloom in mid-season and are characterized by being contracted or partially spread to approximately ¾ inch when in full bloom. At the same time the five petals of the blossoms are of lessor length than the length of petals of the normal showy blossom as exemplified by the 'Loring' (unpatented) peach blossom.

The blossoms of the present peach tree at full bloom may be characterized as being non-showy. More specifically, the blossoms of the present peach tree have radially projecting and angularly spaced five blossom petals to form a blossom having a diameter of about ¾ inch measured across the blossoms.

The flesh of the fruit of the present peach tree is firm and is yellow.

The skin is smooth, having moderate to little down, and is of light red color overlying a yellow ground color. The yellow background covers approximately fifteen percent (15%) of its surface at maturity. At maturity, the peach is spherical having an average diameter of about 2⅝".

The fruit produced by this tree has firm, and non-melting flesh, and thereby has the attendant resistance to blemishes and soft spots in harvesting, shipping and handling due to bruising. The firmness of the fruit flesh is sufficient to allow the flesh to yield and be restored when bumped or dropped without the resulting soft spots as would be experienced in most late season peaches of this market class. Thus, fruit of this tree remains more attractive to the ultimate buyer, the consumer, and thereby will command premium prices for the late fresh desert market.

The fruit matures in the latter part of the peach growing season of southwestern Michigan. The fruit as mentioned heretofore is of light red color overlying a yellow which covers approximately fifteen percent (15%) of its surface and has a very attractive appearance.

BRIEF DESCRIPTION OF THE PHOTOGRAPHS

In the accompanying photographic illustrations, the top photograph taken in the fall, shows a mature second generation tree of average height and width with one remaining peach present on the viewer's lower left side. The photograph was taken on October 1, 2001, and it shows that the peach has remained very firm.

The bottom photograph depicts a whole fruit shown from the top view on the left, and a whole fruit shown from the bottom on the right. In the middle of the photograph is a peach cut in cross section showing that it is freestone, and has clear yellow flesh with red around the pit, which is also red. A tape measure has been placed in the photograph showing that the fiuit from this tree has the genetic capability to exceed three inches (3") in diameter.

DESCRIPTION OF VARIETY

The detailed botanical description of the foliage and fruit of the new variety of peach tree is based upon observation of the specimens grown at Coloma, Mich. with the color terminology, other than the terminology expressed in common terms, in accordance with the Pantone Matching System (PMS) as used internationally to identify printed colors.

Botanical classification: *Prunus persica* cultivar 'P.F. 35-007.'

Tree:

*Age.*—Twelve (12) years.
*Height.*—Unpruned 16'.
*Width.*—Unpruned 12'.
*Size.*—Medium.
*Vigor.*—Medium.
*Density.*—Medium.
*Form.*—More upright than spreading; normally taller than wide. Scaffold branches are strong with little or no bark encroachment in crotches. Trees are easily maintained to have a narrow rounded upright to base-like figure, but are adaptable to other training systems by pruning if desired.
*Production.*—Sizes well with a minimum amount of thinning.
*Bearer.*—Consistent.
*Disease resistance to bacterial leaf and fruit spot.*—Very good.

Trunk:

*Bark.*—Gray (411).
*Size.*—Medium to stocky.
*Suface.*—Medium shaggy.
*Diameter.*—8"— 24" above the ground at 12 years of age.

Branches:

*Size.*—Medium — 2⅜" to 3" at trunk union.
*Surface.*—Smooth to medium.
*Lenticels per square inch on branch.*—Seven (7).
*Lenticel size on branch.*—1/16" to ¼".
*Lenticel color on branch.*—407.
*Branch color.*—Gray (409).
*Crotch angles.*—Tendency towards natural right angles — average 80 degrees.

Leaves:

*Size.*—Medium. Average length — 5" to 6".
*Average width.*—1⅛".
*Form.*—Lanceolate — pointed.
*Thickness.*—Medium.
*Texture.*—Glabrous.
*Margin.*—Serrate.
*Petiole.*—Length, ⅜" — medium thickness.
*Gland.*—0 to 1 on each side of leaf and very small or partial when present.
*Gland color.*—Yellow.
*Gland shape.*—Oval.
*Color.*—Upper surface: green (350c). Bottom: dull green (349c).

Flower buds:

*Size.*—9/16" long, 5/16" wide.
*Shape.*—Ovoid.
*Color.*—243.

Flowers:

*Blooming period.*—May 3, 2001 to May 6, 2001.
*Size of petals.*—½" long, ⅜" wide.
*Shape of petals.*—Cupped.
*Sepal size.*—¼" long, ⅛" wide.
*Sepal shape.*—Cupped.
*Sepal color.*—577.
*Number of anthers.*—34.
*Anther color.*—187.
*Number of stamens.*—34.
*Stamen length.*—⅜".
*Stamen color.*—413.
*Pistil length.*—⅜".
*Pistil color.*—379.
*Pollen.*—Present, self-fertilizing.
*Petal and flower color.*—250.
*Petals per cluster.*—Five (5).
*Flowers per cluster.*—One (1).
*Fragrance.*—Pleasant and strong.

Fruit:

*Maturity when described.*—Firm ripe.
*Date of first picking.*—Sep. 18, 2001 — notably late as compared to ripening dates of all commercial varieties grown in Michigan at current time. Fruit matures very evenly and can be picked in 2 to 3 pickings.
*Date of last picking.*—Last commercial picking was Sep. 24, 2001 — a few peaches were left until Oct. 1, 2001, and were still firm.
*Size.*—Large sphere. 95% of the fruit is 2½" or larger in diameter — over half is 2¾" or larger.
*Form.*—Spherical.
*Suture.*—Medium.
*Weight.*—Average 8.6 oz.

Skin:

*Thickness.*—Medium.
*Texture.*—Medium.
*Tendency to crack.*—None.
*Down.*—Light.
*Color.*—Yellow ground color (120). Nearly overspread (80%) with red (192). Shaded to darker (187).

Flesh:

*Texture.*—Firm — non-melting.
*Ripens.*—Relatively even.
*Flavor.*—Good — a balance between sweet and acid.
*Aroma.*—Pleasant.

*Eating quality.*—Excellent and very juicy.
*Color.*—Yellow with pink cast (155) — pit cavity red (192).

Stone:
*Type.*—Freestone.
*Size.*—Average length — 1½". Average width — 1¼".
*Average thickness.*—⅝".
*Form.*—Ovid.
*Base.*—Straight.
*Apex.*—Notably pointed.
*Sides.*—Notably unequal.
*Surface.*—Irregularly furrowed.
*Color.*—Reddish brown (193).
*Tendency to crack.*—None.
*Kernel.*—¾" long, ½" wide, ⅛" thick.

Use: Desert.
Shipping quality: Excellent.
Keeping quality: Good.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree, substantially as herein illustrated and described.

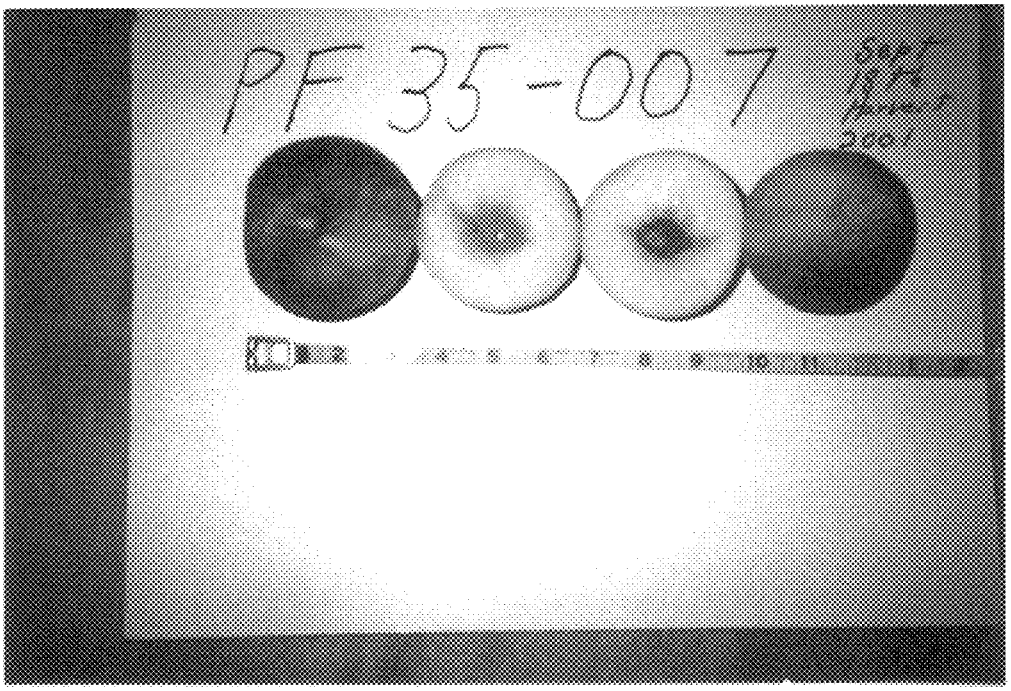
PF 35-007
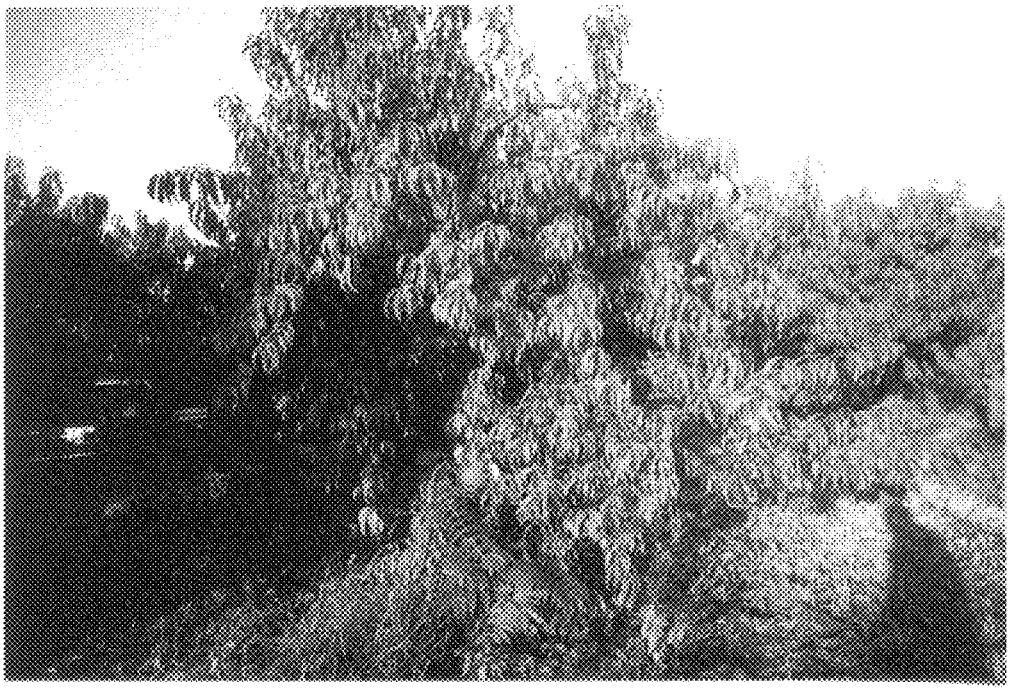

* * * * *